(12) United States Patent
Iott et al.

(10) Patent No.: US 10,595,909 B2
(45) Date of Patent: Mar. 24, 2020

(54) ORTHOPEDIC CLAMP AND EXTENSION ROD

(71) Applicant: GLOBUS MEDICAL, INC., Audubon, PA (US)

(72) Inventors: Andrew Iott, Newtown Square, PA (US); Adam Friedrich, Cinnaminson, NJ (US); Douglas Cahill, Lititz, PA (US); Brad Juchno, Yardley, PA (US); Mark Salzberger, Sinking Spring, PA (US)

(73) Assignee: GLOBUS MEDICAL, INC., Audubon, PA (US)

( * ) Notice: Subject to any disclaimer, the term of this patent is extended or adjusted under 35 U.S.C. 154(b) by 142 days.

(21) Appl. No.: 15/722,440

(22) Filed: Oct. 2, 2017

(65) Prior Publication Data

US 2018/0021066 A1    Jan. 25, 2018

Related U.S. Application Data

(63) Continuation of application No. 14/977,682, filed on Dec. 22, 2015, now Pat. No. 9,808,293, which is a continuation of application No. 14/508,178, filed on Oct. 7, 2014, now Pat. No. 9,283,003, which is a continuation of application No. 12/416,175, filed on Apr. 1, 2009, now Pat. No. 8,882,803.

(51) Int. Cl.
*A61B 17/70*    (2006.01)

(52) U.S. Cl.
CPC ........ *A61B 17/705* (2013.01); *A61B 17/7002* (2013.01)

(58) Field of Classification Search
CPC ....................................... A61B 17/7049–7052
See application file for complete search history.

(56) References Cited

U.S. PATENT DOCUMENTS

| | | |
|---|---|---|
| D301,832 S | 6/1989 | Hathaway |
| 4,875,471 A | 10/1989 | Lea Plaza |
| 5,002,542 A | 3/1991 | Frigg |
| 5,176,680 A | 1/1993 | Vignaud |
| 5,209,752 A | 5/1993 | Ashman |
| 5,306,275 A | 4/1994 | Bryan |
| 5,366,455 A | 11/1994 | Dove |
| 5,466,237 A | 11/1995 | Byrd et al. |
| 5,609,592 A | 3/1997 | Brumfield et al. |
| 5,743,911 A | 4/1998 | Cotrel |
| 5,961,516 A | 10/1999 | Graf |
| 6,004,322 A | 12/1999 | Bernstein |
| 6,086,588 A | 7/2000 | Ameil et al. |

(Continued)

*Primary Examiner* — Jacqueline T Johanas

(57) ABSTRACT

Spinal implants and methods of extending pre-existing spinal implant constructs. An extension clamp may be connected to an original spinal implant including an elongated rod attached to a portion of the spine without removal of the original spinal implant. The extension clamp may include a yoke and an extension rod extending from the yoke. The yoke may include a first end and a second end, the first end having first and second rod engaging portions and a channel between the first and second rod engaging portions for encompassing a fastener, and the second end being spaced apart from the first end. The first and second rod engaging portions may be configured and dimensioned to secure the extension clamp to the elongated rod.

16 Claims, 8 Drawing Sheets

(56) References Cited

U.S. PATENT DOCUMENTS

| | | | |
|---|---|---|---|
| 6,187,005 B1 | 2/2001 | Brace et al. | |
| 6,485,491 B1 | 11/2002 | Farris et al. | |
| 6,565,567 B1 | 5/2003 | Haider | |
| 6,660,004 B2 | 12/2003 | Barker et al. | |
| 6,733,502 B2 | 5/2004 | Altarac et al. | |
| 7,166,109 B2 | 1/2007 | Biedermann et al. | |
| 7,699,872 B2 | 4/2010 | Farris | |
| D622,395 S | 8/2010 | Iott | |
| 7,867,255 B2* | 1/2011 | Miller | A61B 17/705 606/250 |
| 7,947,066 B2* | 5/2011 | Tepper | A61B 17/7052 606/278 |
| 8,021,399 B2 | 9/2011 | Ritland | |
| 8,882,803 B2* | 11/2014 | Iott | A61B 17/7002 606/246 |
| 9,283,003 B2* | 3/2016 | Iott | A61B 17/7002 |
| 9,579,126 B2* | 2/2017 | Zhang | A61B 17/701 |
| 9,808,293 B2* | 11/2017 | Iott | A61B 17/7002 |
| 9,980,755 B2* | 5/2018 | Murray | A61B 17/7052 |
| 2002/0052603 A1* | 5/2002 | Nichols | A61B 17/7052 606/914 |
| 2004/0153070 A1 | 8/2004 | Barker | |
| 2004/0254577 A1 | 12/2004 | Delecrin | |
| 2005/0010215 A1 | 1/2005 | Delecrin | |
| 2005/0137594 A1 | 6/2005 | Doubler | |
| 2005/0182409 A1 | 8/2005 | Callahan et al. | |
| 2005/0234451 A1 | 10/2005 | Markworth | |
| 2005/0240181 A1 | 10/2005 | Boomer et al. | |
| 2006/0009766 A1 | 1/2006 | Lee | |
| 2006/0079872 A1 | 4/2006 | Eggleston | |
| 2006/0079892 A1 | 4/2006 | Roychowdhury | |
| 2006/0084989 A1 | 4/2006 | Dickinson et al. | |
| 2006/0106380 A1 | 5/2006 | Colleran et al. | |
| 2006/0129149 A1 | 6/2006 | Iott | |
| 2006/0129239 A1 | 6/2006 | Kwak | |
| 2006/0149244 A1 | 7/2006 | Amrein et al. | |
| 2007/0043355 A1 | 2/2007 | Wisnewski et al. | |
| 2007/0043365 A1 | 2/2007 | Ritland | |
| 2007/0233089 A1 | 10/2007 | DiPoto | |
| 2007/0233090 A1 | 10/2007 | Naifeh | |
| 2007/0233091 A1 | 10/2007 | Naifeh | |
| 2007/0270805 A1 | 11/2007 | Miller | |
| 2008/0009862 A1 | 1/2008 | Hoffman | |
| 2008/0045955 A1 | 2/2008 | Berrevoets et al. | |
| 2008/0249570 A1 | 10/2008 | Carson et al. | |
| 2008/0262553 A1 | 10/2008 | Hawkins | |
| 2008/0294197 A1 | 11/2008 | Egli | |
| 2008/0294203 A1 | 11/2008 | Kovach et al. | |
| 2009/0043339 A1 | 2/2009 | Tepper | |
| 2009/0093843 A1 | 4/2009 | Lemoine | |
| 2009/0118765 A1 | 5/2009 | Muller | |
| 2009/0182376 A1 | 7/2009 | Iott | |
| 2009/0210007 A1 | 8/2009 | Levy | |
| 2009/0228043 A9 | 9/2009 | Egli | |
| 2010/0036425 A1 | 2/2010 | Barrus | |
| 2010/0249843 A1 | 9/2010 | Wegrzyn | |
| 2012/0010664 A1 | 1/2012 | Ritland | |
| 2013/0018421 A1* | 1/2013 | George | A61B 17/7044 606/278 |

* cited by examiner

ORTHOPEDIC CLAMP AND EXTENSION ROD

CROSS-REFERENCE TO RELATED APPLICATIONS

This application is a continuation of U.S. application Ser. No. 14/977,682, filed Dec. 22, 2015, which is a continuation of U.S. application Ser. No. 14/508,178, filed Oct. 7, 2014, now U.S. Pat. No. 9,283,003, which is a continuation of U.S. application Ser. No. 12/416,175, filed Apr. 1, 2009, now U.S. Pat. No. 8,882,803, the contents of which are incorporated by reference herein in their entireties for all purposes.

All publications and patent applications mentioned in this specification are herein incorporated by reference to the same extent as if each individual publication or patent application was specifically and individually indicated to be incorporated by reference.

FIELD OF THE INVENTION

The present invention relates to a spinal implant that stabilizes and supports the spine.

BACKGROUND OF THE INVENTION

Spinal deformities, spinal injuries, and other spinal conditions may be treated with the use of spinal implants. Spinal implants are designed to support the spine and properly position the components of the spine. One such spinal implant includes an elongated rod and a plurality of bone anchors. The elongated rod is positioned to extend along one or more of the components of the spine and the bone anchors are attached to the spinal components at one end and secured to the elongated rod at the other end.

However, adjacent segment disease and other conditions may require revisions requiring a surgeon to remove the entire spinal implant and position new implants to further support and stabilize the spinal components of the anatomy. The removal of the original spinal implant and the subsequent positioning of new implants may cause additional problems for the patient and increases the cost and time of spinal surgeries. Therefore, there is a need to provide spinal implants that provide support and stability to the spinal components of the anatomy by reducing the cost and time of the surgery caused by adjacent segment disease and other similar conditions.

Specifically, there is a need for a spinal implant that enables fusion and stability of the spine without removing the original implants, thereby reducing the time and cost of the surgery.

SUMMARY OF THE INVENTION

The present invention provides a spinal implant for connecting to an elongated rod. The spinal implant includes a yoke having a first end and a second end, the first end having a first and second rod engaging portion and a channel between the first and second rod engaging portions for encompassing a first bone anchor, and the second end being spaced apart from the first end. An extension rod is also provided which extends from the second end of the yoke parallel to the elongated rod. The first and second rod engaging portions are configured and dimensioned to receive first and second securing member for securing the elongated rod.

BRIEF DESCRIPTION OF THE DRAWINGS

The invention will be more readily understood with reference to the embodiments thereof illustrated in the attached drawing figures, in which.

DETAILED DESCRIPTION OF THE INVENTION

Embodiments of the invention will now be described. The following detailed description of the invention is not intended to be illustrative of all embodiments. In describing embodiments of the present invention, specific terminology is employed for the sake of clarity. However, the invention is not intended to be limited to the specific terminology so selected. It is to be understood that each specific element includes all technical equivalents that operate in a similar manner to accomplish a similar purpose.

Figure 1:
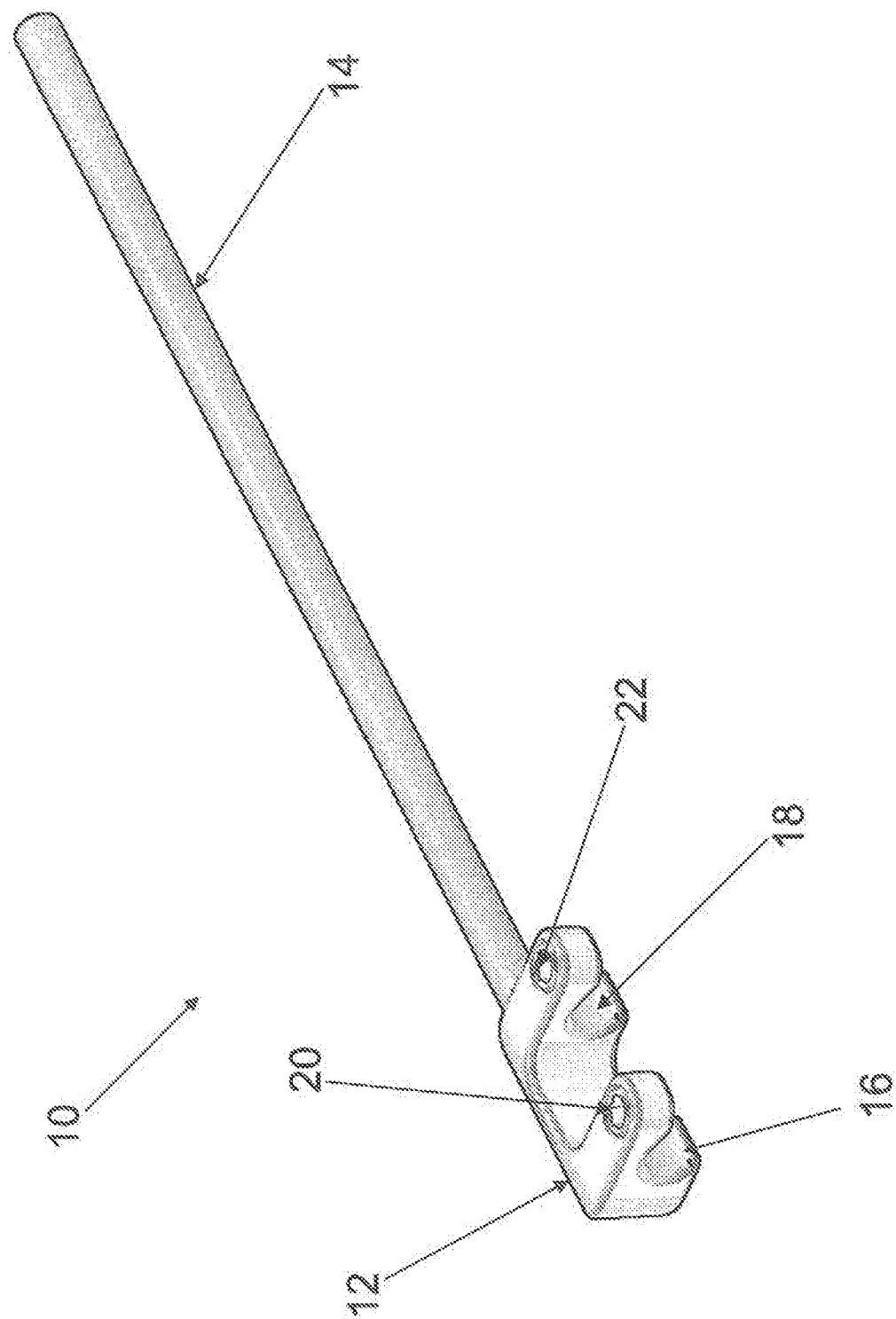
FIG. 1 illustrates the spinal implant according to the present invention.
Figure 2:
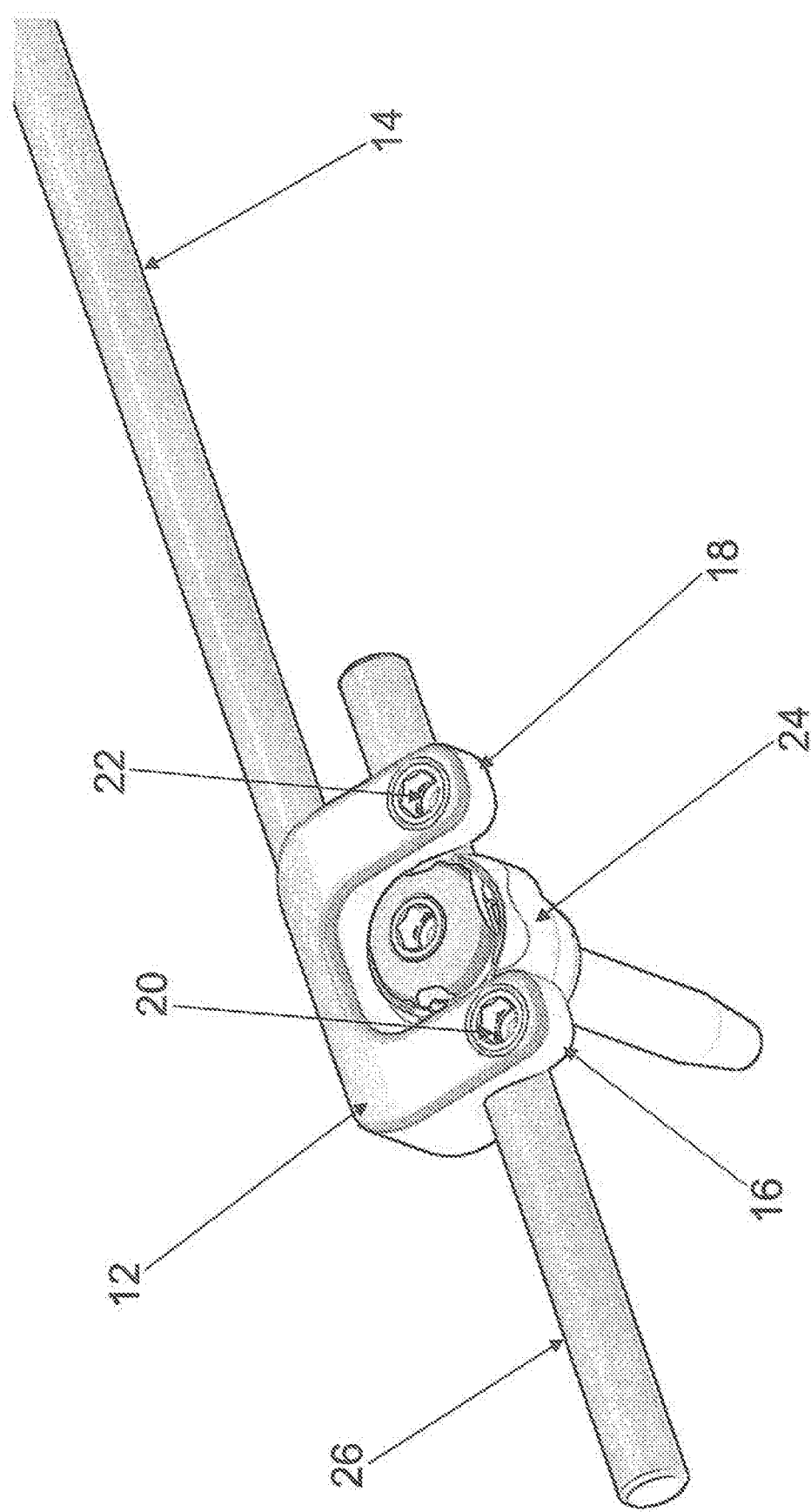
FIGS. 2-5 illustrate different views of the spinal implant in combination with a rod and screw system.
Figure 3:
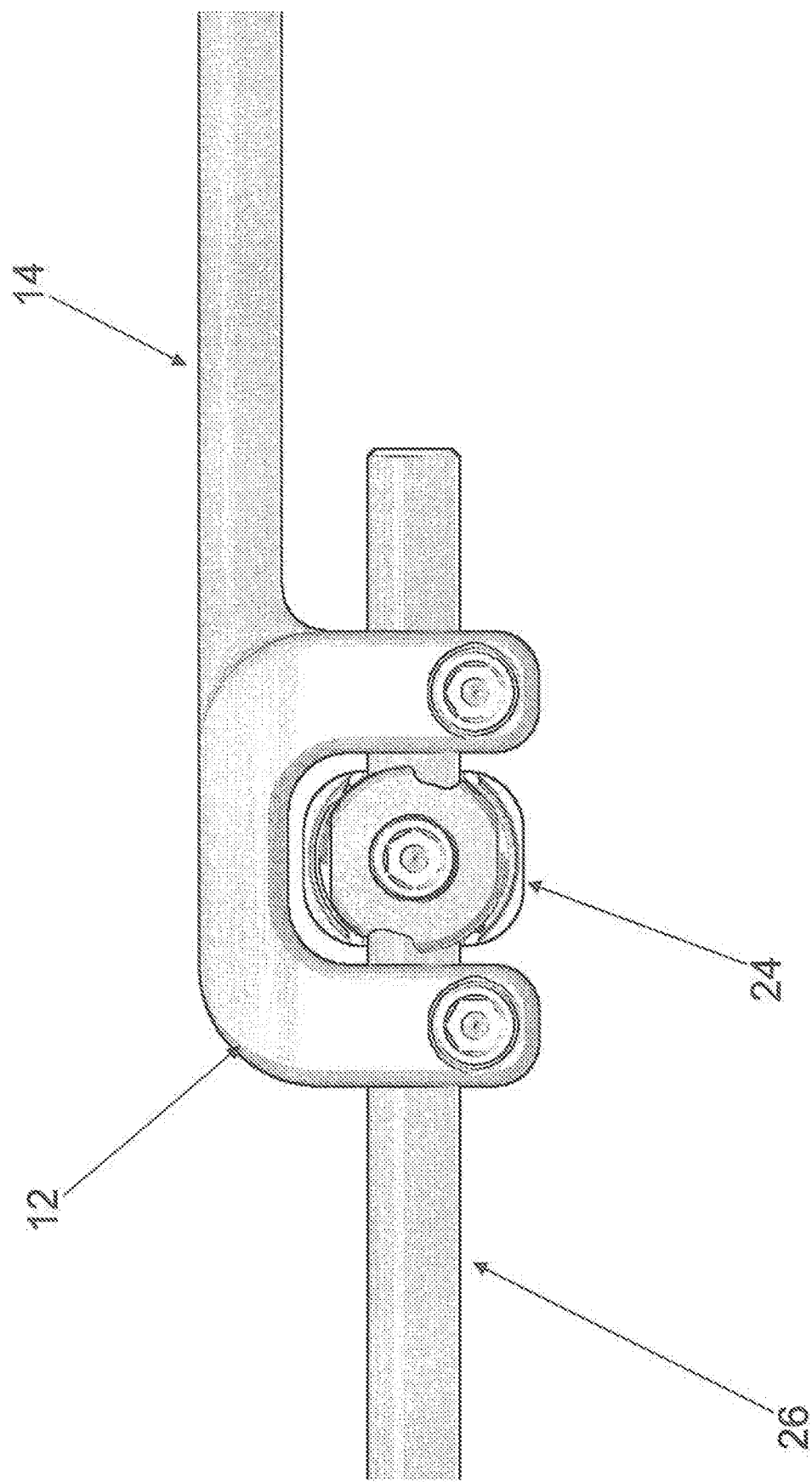
Figure 4:
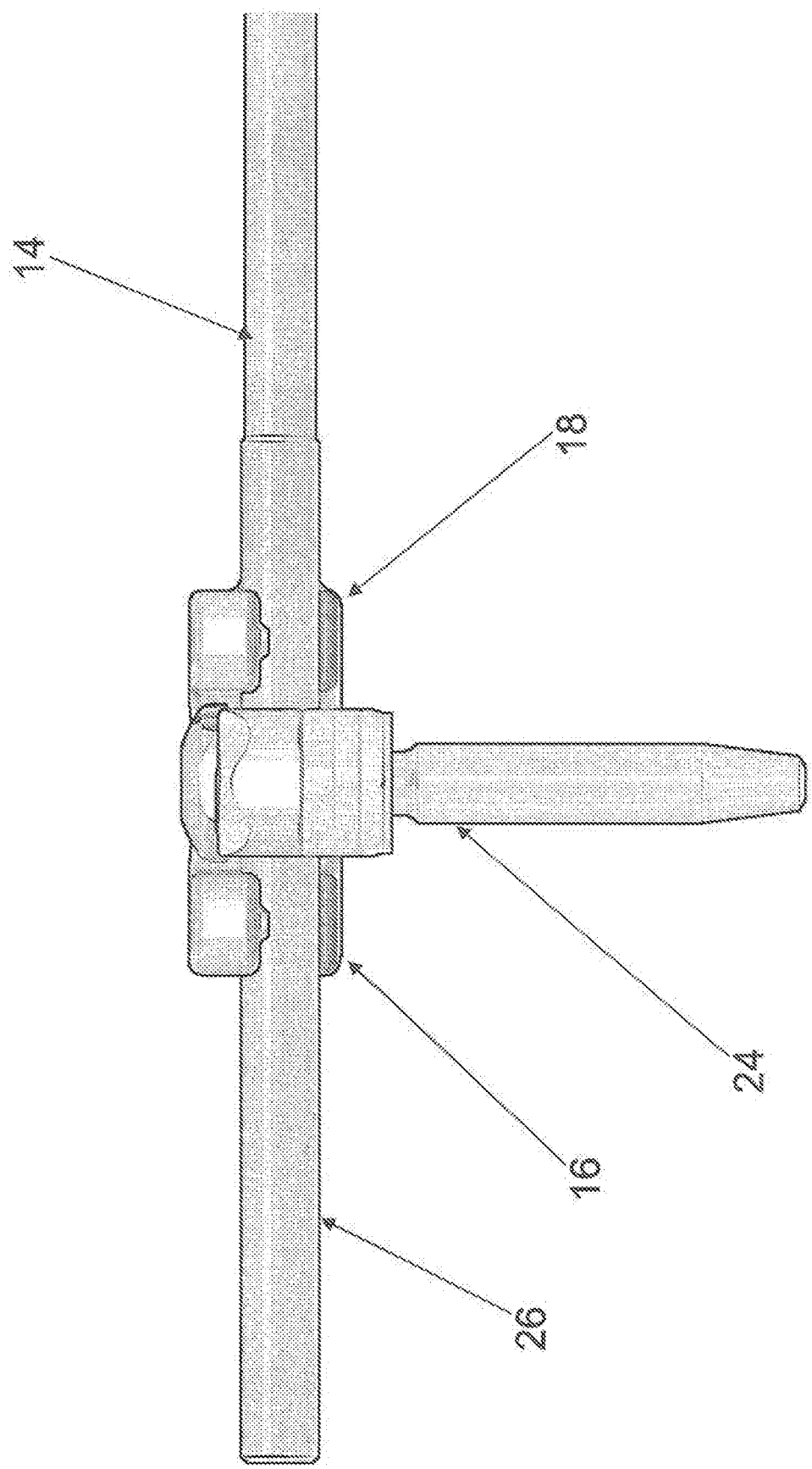
Figure 5:
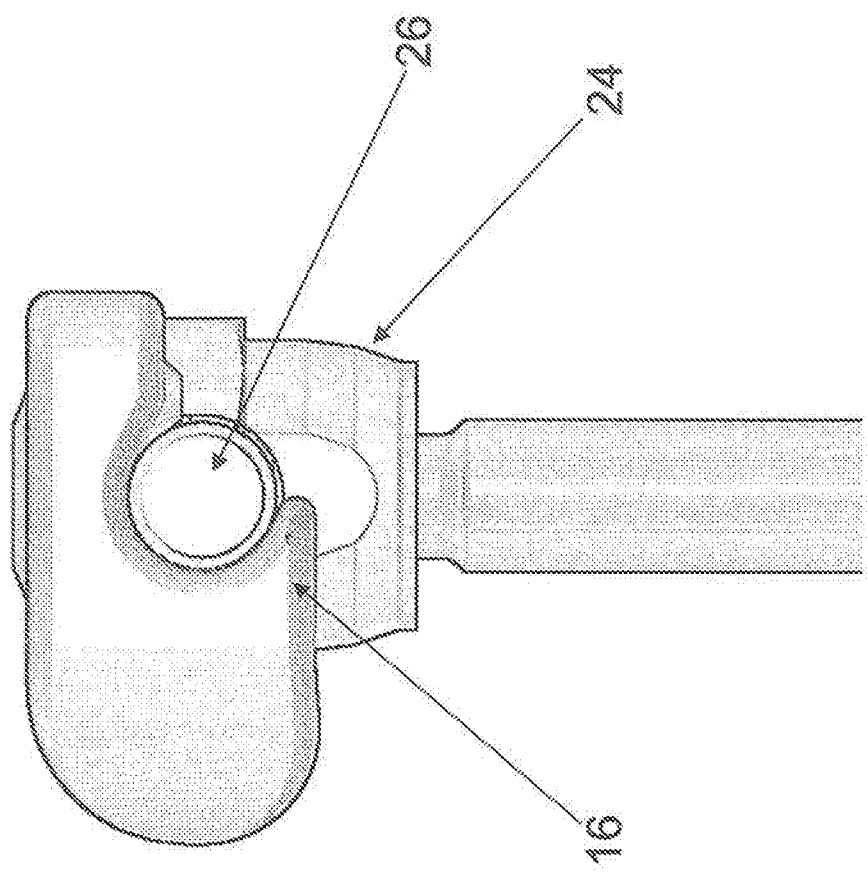
Figure 6:
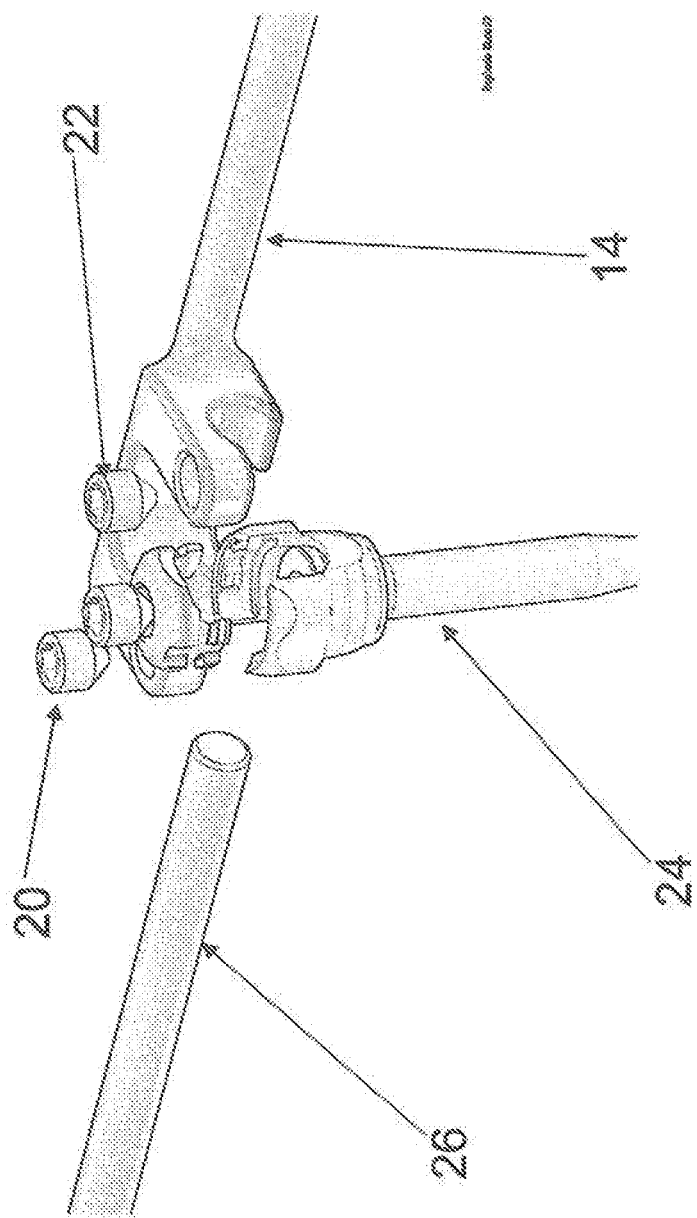
FIG. 6 is an exploded view of the implant system according to the present invention.

FIG. 1 illustrates the extension clamp 10 according to one embodiment of the present invention. The clamp 10 as shown is configured and dimensioned having a yoke 12 and an integrated rod 14. As clearly illustrated in FIG. 1, the yoke 12 and the rod 14 of the clamp 10 are integrated as a single piece. The yoke 14 is merged or integrated with the rod 12 that is preferably 160 millimeters long and having a diameter of 5.5 millimeters. However, the rod 12 may be shaped and sized to fit a patient's anatomy and any requirements to enhance the stability of the fusion fixation system. The clamp 10 is configured to connect to a rod and screw system as illustrated in FIGS. 2-6. The yoke 12 of the clamp 10 is also configured with a first and second rod engaging portions 16 and 18 for engaging with the rod. Each of the first and second rod engaging portions 16 and 18 are provided with first and second securing members 20, 22 for locking the clamp 10 onto the rod. The channel between the first and second rod engaging portions is dimensioned to encompass a fastening element such as a bone anchor or pedicle screw, which is more clearly illustrated in FIGS. 2-6.

Figure 7:
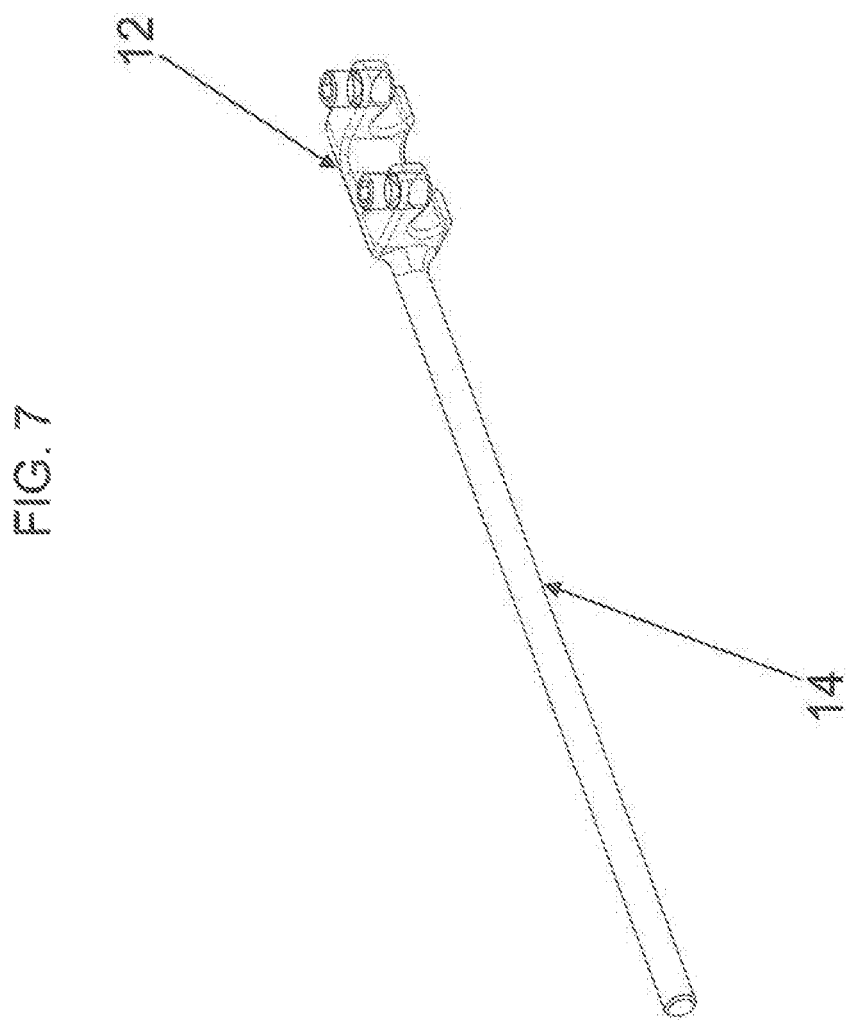
FIG. 7 illustrates another embodiment of the present invention.

FIGS. 2-6 illustrate the connection of the extension clamp 10 to a fastener/screw 24 and rod 26. As shown in FIGS. 2-6, the first and second engaging portions 16 and 18 of the yoke 12 engages with rod 26. The bone anchor which is attached to the honey elements of the spine and which captures and retains the rod 26 is fit within the channel of the yoke 12. The yoke 12 encompasses the bone anchor and secured to the rod 26 through the first and second securing members 20, 22. The clamp 10 being connected to the rod 26 and surrounding the bone fastener provides additional stability to the spine since the integrated rod 14 of the clamp 10 is attached to a bone element of the spine at an adjacent level segment through an another bone anchor. The integrated rod 14 as shown is spaced apart from the rod 26 that is coupled to the yoke 12 of the clamp 10. The integrated rod 14 is in a parallel axis to the connected rod 26. In this particular embodiment, the integrated rod 14 is illustrated to extend from one end of the clamp 10 spaced apart from the yoke 12. However, the integrated rod can be configured in various different designs, such as the integrated rod 14 extending from the a second end of the clamp spaced apart from the yoke as illustrated in FIG. 7.

Although a set screw is illustrated for coupling the clamp with the rod 26, any type of securing member can be used including, but not limited to, a bolt, a pin, a shoe, an interference member, or a cam member. In an exemplary embodiment, the securing member includes a coupling for engaging a driver or other device for threading the securing member into the second opening.

The integrated rod 14 is configured and dimensioned to be received and captured by a fastener which is attached to a pedicle or another bony element of the spine. The system allows a surgeon to reduce the amount of time in surgery as well as providing additional stability and support when enhancing fusion between vertebrae.

Figure 8:
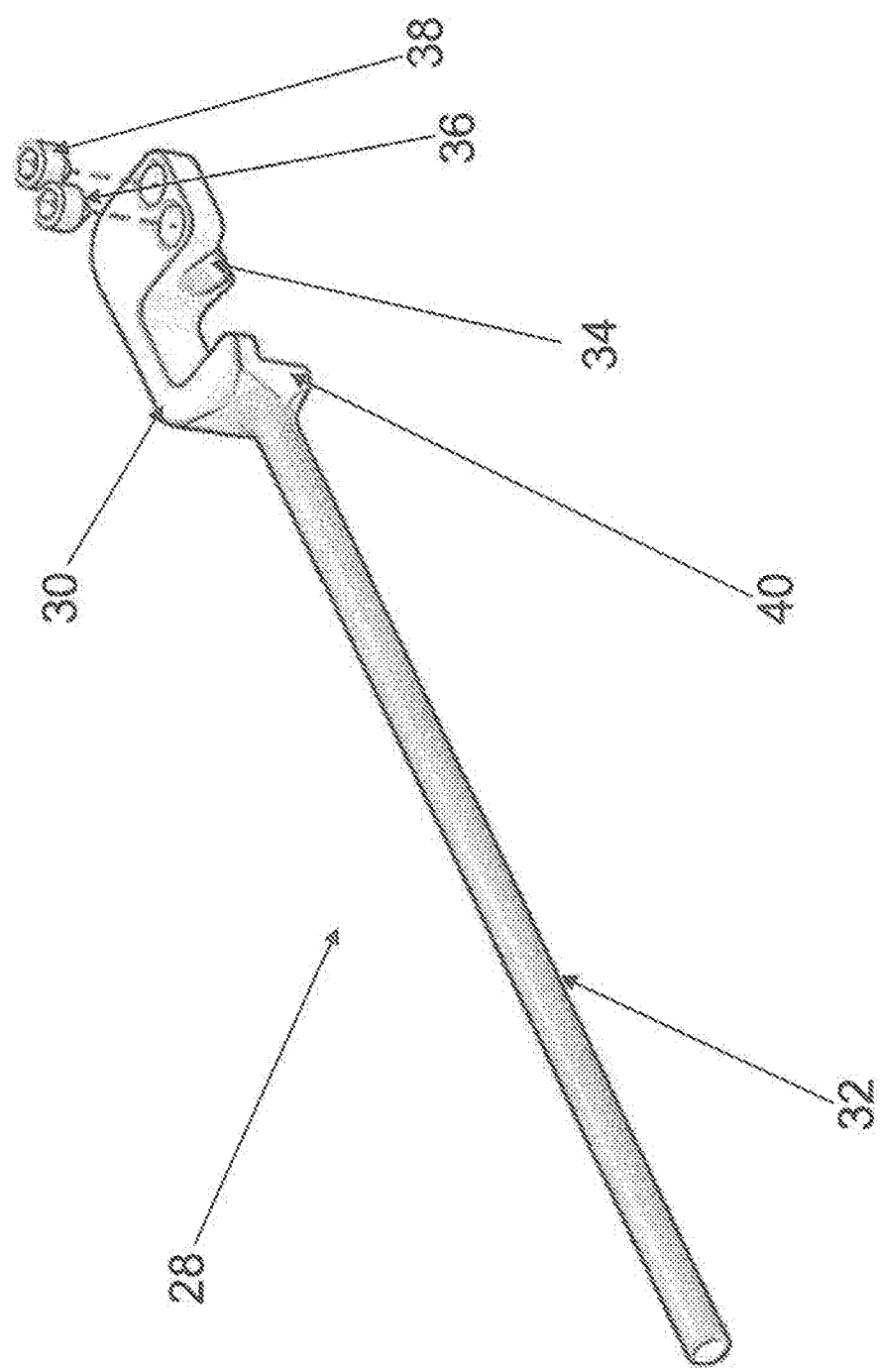
FIG. 8 illustrates yet another embodiment of the present invention.

FIG. 8 illustrates another embodiment of the present invention. In this particular embodiment, the clamp 28 is configured and dimensioned to be attached to a rod in in-line axis. The clamp 28 is provided with a yoke 30 and an inline integrated rod 32. The clamp 28 is secured to a rod (not shown) by the rod engaging portion 34 of the yoke 30. The yoke 30 is secured to the rod through securing members 36 and 38. One end of the rod is situated at the other end 40 of the yoke 30. As noted above, any type of securing element may be used to secure the rod to the clamp according the present invention.

Example embodiments having the components of the present invention have been described herein. As noted, these example embodiments having been described for illustrative purposes only, and are not limiting. Other embodiments are possible and are covered by the invention. Such embodiments will be apparent to persons skilled in the relevant art based on the teachings contained herein. Thus, the breadth and scope of the present invention should not be limited by any of the above-described exemplary embodiments, but should be defined only in accordance with the following claims and their equivalents.

What is claimed is:

1. A surgical system comprising:
an extension clamp including a yoke having a first end and a second end, the yoke comprising first and second rod engaging portions and a channel between the first and second rod engaging portions, the second end being spaced apart from the first end, and an extension rod extending from the second rod engaging portion; and
a fastener received in the channel, wherein the fastener comprises a head and a shaft, wherein the head is sized smaller than a length of the channel and wherein the shaft is configured to extend into a bone member, and
wherein the extension rod and the yoke are integrated as a single piece, and
wherein the extension clamp further comprises a first securing member and a second securing member, wherein the first securing member is received through an upper surface of the first rod engaging portion and the second securing member is received through an upper surface of the second rod engaging portion.

2. The surgical system of claim 1, wherein the extension clamp is connected to an elongated rod.

3. The surgical system of claim 2, wherein the first securing member and second securing member contact the elongated rod.

4. The surgical system of claim 3, wherein the first securing member is a first set screw and the second securing member is a second set screw.

5. The system of claim 1, wherein the head of the fastener comprises a third securing member.

6. The surgical system of 1, wherein the bone member that the shaft is configured to extend into is a pedicle.

7. The system of claim 1, wherein the first and second rod engaging portions are hook type elements.

8. The system of claim 1, further comprising an elongated rod that is configured and dimensioned to be captured and retained within the fastener.

9. A surgical system comprising:
an extension clamp including a yoke having a first end and a second end, the yoke comprising first and second rod engaging portions and a channel between the first and second rod engaging portions, and an extension rod extending from the second rod engaging portion; and
a fastener received in the channel, wherein the fastener comprises a head and a shaft, wherein the head is sized smaller than a length of the channel and wherein the shaft is configured to extend into a bone member, and
wherein the extension rod and the yoke are integrated as a single piece, and
wherein the extension clamp further comprises a first securing member and a second securing member, wherein the first securing member is received through an upper surface of the first rod engaging portion and the second securing member is received through an upper surface of the second rod engaging portion.

10. The system of claim 9, further comprising an elongate rod attachable to the extension clamp.

11. The system of claim 10, wherein, once connected, the extension rod is offset relative to the existing elongated rod.

12. The surgical system of claim 9, wherein the extension clamp is connected to an elongated rod via the first securing member and the second securing member.

13. The surgical system of claim 12, wherein the first securing member is a first set screw and the second securing member is a second set screw.

14. The system of claim 13, wherein the head of the fastener comprises a third securing member.

15. The surgical system of 9, wherein the bone member that the shaft is configured to extend into is a pedicle.

16. The system of claim 9, wherein the first and second rod engaging portions are hook type elements.

* * * * *